United States Patent [19]

Brown

[11] Patent Number: 4,598,050
[45] Date of Patent: Jul. 1, 1986

[54] CULTURE PLATE FOR SURFACES

[76] Inventor: Lewis R. Brown, 5 Hialeah Dr., Starkville, Miss. 39759

[21] Appl. No.: 557,447

[22] Filed: Dec. 2, 1983

[51] Int. Cl.⁴ .............................................. C12M 1/22
[52] U.S. Cl. ..................................... 435/298; 435/301
[58] Field of Search ................... 435/30, 31, 297, 298, 435/299, 300, 301

[56] References Cited
U.S. PATENT DOCUMENTS

| | | | |
|---|---|---|---|
| 3,630,849 | 12/1971 | Land et al. | 435/297 |
| 3,751,341 | 5/1975 | Seitz et al. | 435/30 |
| 4,326,028 | 4/1982 | Brown | 435/30 |

Primary Examiner—Sam Rosen
Assistant Examiner—William J. Herald
Attorney, Agent, or Firm—Ferris M. Stout

[57] ABSTRACT

An easily loaded culture plate for microorganisms with an unconstrained flat agar surface for sampling flat areas.

4 Claims, 2 Drawing Figures

CULTURE PLATE FOR SURFACES

BACKGROUND

1. Field of the Invention

The invention is in the field of microbial assaying apparatus.

2. The Prior Art

Determining the number of microorganisms on a flat surface—an operating table, a restaurant counter, a work bench in a food processing plant, for example—presents a problem to microbiologists. One way to make this measurement is to swab the surface in question with a moist sterile swab, and then streak the surface of a sterile nutrient medium with the swab. Alternatively the swab is rinsed in a known volume of sterile broth and then a conventional plate count is done on the broth. Neither method yields a result which is a dependably quantitative measure of the contamination actually present on the surface, because one cannot be sure that all of the microorganisms collected on the swab were transferred to the culture. Moreover these methods are tediously time consuming.

Another method for determining the numbers of microbes on a surface involves the use of contact agar plates. The RODAC (tm) Plate (made and sold by BBL division of Becton, Dickinson & Co.) is an example. In this method plates of solid nutrient medium are provided in which an agar surface protrudes slightly above the rim of the bottom half of a petri plate. To use the RODAC(tm), one removes the lid and gently presses the surface of the protruding nutrient medium onto the test surface. The lid is replaced and the exposed plate is incubated. Colonies developing on the medium surface are counted, and the density of microorganisms on the surface being tested is calculated.

Although, relative to the swab method, the RODAC plate method is quick, it too has serious drawbacks. To prepare a RODAC plate one must overfill it with melted agar, depending on a meniscus to hold the level of liquid agar above the plate rim until it gels—a tricky business with frequent spillovers, which wastes time and expensive agar. Also, the agar surface which protrudes from the top of the plate tends to be dimpled, or partly concave; in use, special attention is required to ensure complete contact of the agar surface with the test surface.

The requirement that the agar surface be quite flat is recognized in U.S. Pat. No. 3,630,849, issued to Land. Land provides a receptacle with a key arrangement in it for holding solidified agar in place, and a tight-fitting bottom lid. When liquid agar which has been poured into Land's receptacle cools, and the bottom lid is removed, the agar surface uncovered is truly planar. The agar surface however is surounded by the lower edges of the receptacle walls. If the surface to be sampled is less than truly flat, the receptacle walls will bridge concavities in the surface; and being rigid, the walls will prevent contact between the surface to be sampled and the flat agar surface.

There exists therefore a need for a surface contact plate which can be prepared in the laboratory by technicians of ordinary skill, and which provides a perfectly flat surface for sampling. The plate of this invention, which is hereafter referred to as the "Surcon Plate", embodies these advantages, as will be made clear below.

SUMMARY OF THE INVENTION (In what follows, "top" and "bottom" refer to the Surcon Plate as it appears when it is in position to have agar poured into it.)

The Surcon Plate comprises a top lid, a first receptacle with a perforated bottom, a second receptacle with an impermeable bottom, and a bottom lid. The first receptacle fits into the top of the second receptacle, forming a leak-tight seal with it, and providing a space between the perforated bottom of the first receptacle and the impermeable bottom of the second receptacle. The bottom lid when in place is separated from the second receptacle's bottom by spacers on the bottom of the latter.

To use the Surcon Plate, I remove the top lid and pour hot agar into the first receptacle. When the agar has cooled and gelled, I remove the bottom lid; then I remove and discard the second receptacle, exposing a perfectly flat agar surface, the gelled agar being supported within the first receptacle by its perforated bottom. It is a simple matter to hold the flat agar surface against another surface to pick up microorganisms for assay, as described above. When the sampling procedure is complete the bottom lid is replaced, preserving the freshly exposed agar surface from extraneous contamination.

DESCRIPTION OF A PREFERRED EMBODIMENT

Please refer now to the drawings.

Figure 1:
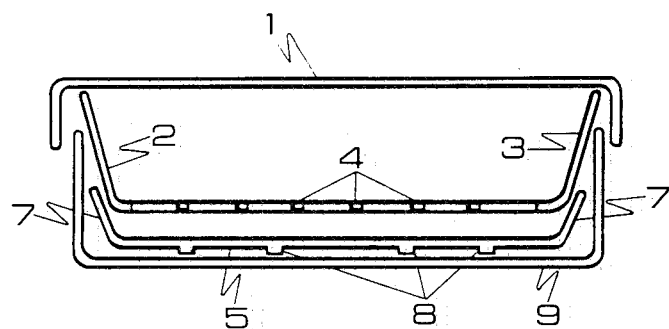
FIG. 1 is a cross-sectional view of an empty Surcon Plate.

FIG. 1 shows a cross-section of a preferred embodiment of the Surcon Plate.

1 is the top lid, similar to the lid of a petri plate. 2 is the first receptacle of the Surcon Plate. Its sides 3 taper downward.

4 is the perforated bottom of first receptacle 2, which holds the agar in place after it has solidified.

5 shows the second receptacle. Its tapered sides 7 sealingly engage the outer surface of the sides 3 of the first receptacle, so that there is a space of 2 mm, more or less, between the bottoms of the two receptacles. Spacers 8 extend from the bottom surface of second receptacle 5, so that when bottom lid 9 is in place, it presses against the spacers, holding the second receptacle 5 in sealing engagement with first receptacle 2.

Figure 2:
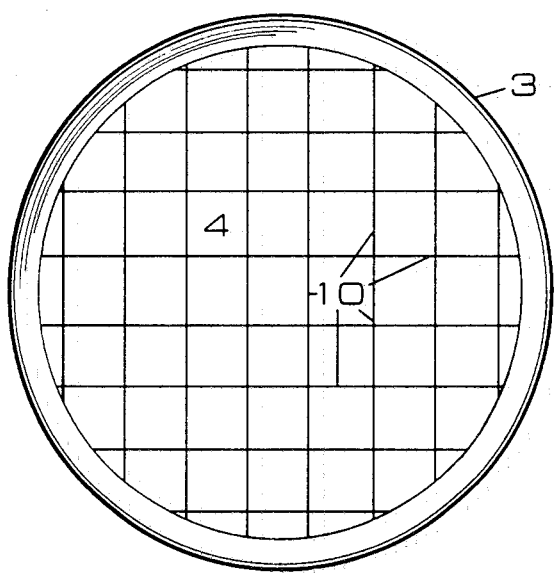
FIG. 2 is a plan view of the Surcon Plate.

In FIG. 2, a plan view of perforated bottom structure 4 which holds the agar in place after it has solidified, is shown. In the preferred embodiment the perforations in the bottom take the form of a grid. The grid may be of any pattern which will allow liquid agar to flow through it; but I have found it useful to space grid supports 10 one centimeter apart to facilitate the counting of colonies growing on the agar bed which the perforated bottom supports.

In an alternate embodiment (not shown) the bottom of the first receptacle is a flat plate with one or more holes in it to allow liquid agar to flow into the second receptacle before the agar gels.

The description of this preferred embodiment is only illustrative of the invention; it is not to be construed as limiting the scope of the invention, which is as defined in the claims.

What is claimed is:

1. In a device for collecting microorganisms from surfaces and culturing them comprising
   a top lid,
   a first receptacle with a rim and having an agar-holding structure and agar flow-through means in it,
   a second receptacle with a rim and a flat, impermeable bottom, and
   a bottom lid,
the improvement which comprises
   means for joining the first receptacle to the second receptacle whereby, when melted agar is poured into the first receptacle and allowed to solidify, a flat agar surface which extends beyond the bottom of the first receptacle is formed.

2. In an agar-containing assembly of the type having
   a top lid,
   a first receptacle having a rim and having an agar-holding structure in it, so that liquified agar, when poured into the receptacle and allowed to solidify, forms a plug of agar with a perimeter and a surface orthogonal to the perimeter,
   a second receptacle with a rim and a flat, impermeable bottom, and
   a bottom lid,
the improvement which comprises
   sealing means between the first receptacle and the second receptacle which forms the agar plug so that the plug has a true flat surface, the perimeter of which is unconstrained within at least one millimeter of the rim of the first receptacle.

3. In an agar-containing assembly of the type having
   a top lid,
   a first receptacle having side walls with a bottom edge and having an agar-holding structure in it,
   a second receptacle with side walls with a top edge, and a flat, impermeable bottom,
   sealing means which seals the first receptacle to the second receptacle, and
   a bottom lid,
the improvement which comprises
   axial spacing means between the sealing means and the bottom edge of the first receptacle's side walls.

4. The assembly of claim 3 in which the side walls of the first receptacle taper toward its bottom edge, and, when the second receptacle is placed over the bottom of the first receptacle, the side walls of the second receptacle are of a size which sealingly engage the outer surface of the first receptacle walls before the bottom of the second receptacle can contact the bottom edge of the first receptacle.

* * * * *